(12) United States Patent
Millerd et al.

(10) Patent No.: US 8,216,187 B2
(45) Date of Patent: Jul. 10, 2012

(54) SAFETY CATHETER

(75) Inventors: Don Millerd, San Diego, CA (US); Hooman A. Asbaghi, San Diego, CA (US)

(73) Assignee: Millaghi Medical, Inc., San Diego, CA (US)

( * ) Notice: Subject to any disclaimer, the term of this patent is extended or adjusted under 35 U.S.C. 154(b) by 106 days.

(21) Appl. No.: 12/494,108

(22) Filed: Jun. 29, 2009

(65) Prior Publication Data

US 2010/0331781 A1    Dec. 30, 2010

(51) Int. Cl.
*A61M 5/178* (2006.01)

(52) U.S. Cl. ......... 604/164.12; 604/164.01; 604/168.01; 604/167.03

(58) Field of Classification Search ............ 604/164.12, 604/110, 164.08, 48, 93.01, 164.01, 164.06, 604/164.07, 167.01–167.05, 168.01
See application file for complete search history.

(56) References Cited

U.S. PATENT DOCUMENTS

| | | |
|---|---|---|
| 4,723,946 A | 2/1988 | Kay |
| 5,053,014 A * | 10/1991 | Van Heugten ........... 604/167.03 |
| 5,104,384 A | 4/1992 | Parry |
| 5,267,972 A | 12/1993 | Anderson |
| 5,292,314 A | 3/1994 | D'Alessio et al. |
| 5,376,080 A | 12/1994 | Petrussa |
| 5,389,085 A | 2/1995 | D'Alessio et al. |
| 5,403,283 A | 4/1995 | Luther |
| 5,403,286 A | 4/1995 | Lockwood |
| 5,562,629 A | 10/1996 | Haughton et al. |
| 5,578,011 A | 11/1996 | Shaw |
| 5,683,368 A | 11/1997 | Schmidt |
| 5,700,250 A | 12/1997 | Erskine |
| 5,713,876 A | 2/1998 | Bogert et al. |
| 5,817,058 A | 10/1998 | Shaw |
| 5,853,393 A | 12/1998 | Bogert |
| 5,935,102 A | 8/1999 | Bowden et al. |
| 5,989,220 A * | 11/1999 | Shaw et al. ................... 604/110 |
| 6,050,976 A | 4/2000 | Thorne et al. |
| 6,436,070 B1 | 8/2002 | Botich et al. |
| 6,475,189 B1 | 11/2002 | Lilley, Jr. |
| 6,530,905 B2 | 3/2003 | Asbaghi |
| 6,582,402 B1 | 6/2003 | Erskine |
| 6,626,864 B2 | 9/2003 | Jansen |
| 6,958,054 B2 | 10/2005 | Fitzgerald |
| 7,198,617 B2 | 4/2007 | Millerd |
| 7,229,421 B2 | 6/2007 | Jen et al. |
| 7,344,516 B2 | 3/2008 | Erskine |
| 7,422,572 B2 | 9/2008 | Popov et al. |
| 7,604,616 B2 | 10/2009 | Thoresen et al. |

(Continued)

FOREIGN PATENT DOCUMENTS

EP    0847289 B1    6/1998

(Continued)

*Primary Examiner* — Christopher D Koharski
*Assistant Examiner* — Leah Stohr
(74) *Attorney, Agent, or Firm* — Nydegger & Associates

(57) ABSTRACT

A device and method for positioning a catheter to establish a fluid access site into the vasculature of a patient includes a luer assembly that incorporates the catheter. Also included is a shuttle assembly that has a stylet for stiffening the catheter. In combination, the stiffened catheter and the shuttle assembly are held on a handle by the interaction of the luer assembly with the handle. Once the stiffened catheter is inserted into the vasculature, the luer assembly is separated from the handle and from the stylet, and is left in place. With this separation, the shuttle assembly is also released to be repositioned and concealed within the handle.

5 Claims, 3 Drawing Sheets

U.S. PATENT DOCUMENTS

| | | |
|---|---|---|
| 7,618,396 B2 | 11/2009 | Slate et al. |
| 7,736,340 B2 | 6/2010 | Harding et al. |
| 7,887,549 B2 | 2/2011 | Wenderow et al. |
| 2003/0060760 A1 | 3/2003 | Botich et al. |
| 2003/0199827 A1 | 10/2003 | Thorne |
| 2004/0127854 A1 | 7/2004 | Leinsing et al. |
| 2005/0245875 A1 | 11/2005 | Restelli et al. |
| 2007/0083162 A1 | 4/2007 | O'Reagan et al. |
| 2009/0131872 A1 | 5/2009 | Popov |
| 2009/0177163 A1 | 7/2009 | King et al. |
| 2010/0210934 A1 | 8/2010 | Belson |
| 2010/0256558 A1 | 10/2010 | Olson et al. |

FOREIGN PATENT DOCUMENTS

| | | |
|---|---|---|
| EP | 1689468 B1 | 8/2006 |
| JP | 09192230 A | 7/1997 |
| WO | 0241932 A3 | 5/2002 |
| WO | 2008030999 A3 | 3/2008 |

\* cited by examiner

SAFETY CATHETER

FIELD OF THE INVENTION

The present invention pertains generally to medical catheters. More specifically, the present invention pertains to devices that position the cannula of a catheter in fluid communication with the vasculature of a patient to establish a single fluid access site for repetitive or sequential use with an extracorporeal fluid source. The present invention is particularly, but not exclusively, useful as a device for manipulating a stylet to position a catheter in fluid communication with the vasculature of a patient, and for subsequently concealing the stylet, to thereby prevent inadvertent "sticks" with the stylet after it has been removed from the catheter.

BACKGROUND OF THE INVENTION

Fluid access into the vasculature of a patient may be necessary, or desirable, for any of several different reasons. In the event, a fluid flow path must somehow be established between an extracorporeal fluid source and the vasculature. Moreover, when an infusion protocol is involved that requires periodic injections, an established fluid access site that can be repetitively used for a sequence of different injections may be required. Establishing such an access site, however, can be problematical.

When a catheter is used to establish a fluid access site into the vasculature of a patient, the catheter itself (i.e. its cannula) is preferably flexible. The flexible catheter, however, needs to first be somehow stiffened so its distal end can be passed through tissue and thus positioned in the vasculature. Typically, this stiffening is accomplished using a stylet that can be selectively inserted into the lumen of the catheter. After the stiffened catheter has been properly positioned in the vasculature, the stylet must then be removed from the catheter to leave the catheter in fluid communication with the vasculature. Preferably, this separation of the catheter from the stylet is accomplished as easily as possible. Furthermore, once the stylet has been removed from the catheter, it becomes necessary to protect the user from inadvertent or accidental "sticks" by the sharp end of the stylet.

In light of the above, it is an object of the present invention to provide a safety catheter that can be properly positioned, with its distal end in the vasculature of a patient, to thereby establish a single fluid access site for multiple infusions of a fluid medicament into the vasculature from an extracorporeal fluid source(s). Another object of the present invention is to provide a safety catheter that can, in a single-step operation, be separated from a stiffening stylet with an automatic concealment of the stylet to prevent inadvertent or accidental "sticks" by the sharp end of the stylet. Yet another object of the present invention is to provide a safety catheter that is easy to manufacture, is simple to use, and is comparatively cost effective.

SUMMARY OF THE INVENTION

In accordance with the present invention, a safety catheter is provided that is operationally prepared for immediate insertion into the vasculature of a patient. Specifically, the intent is to establish a single fluid access site into the vasculature of the patient that can be repetitively or sequentially used by extracorporeal fluid sources (e.g. a hypodermic syringe or IV pump). For the present invention, the positioning of the safety catheter is accomplished using a dedicated device. The functionality of this dedicated device is essentially two-fold. For one, the device is initially used to stiffen the catheter with a stylet. This is done so the otherwise flexible cannula of the catheter can be effectively inserted and positioned in the patient's vasculature. For another, once the catheter is positioned, the device is engineered to automatically withdraw the stylet from the catheter, and to simultaneously conceal the stylet so its sharp end will not inadvertently or accidentally "stick" the user or some other third person.

Structurally, the safety catheter essentially has three components. They are: a handle, a luer assembly, and a shuttle assembly. Considering each component separately, the handle of the safety catheter includes an elongated handle body that has a proximal end and a distal end. It is also formed with an internal chamber that extends between the two ends. Further, the handle includes a hollow, cylindrical-shaped body top having a proximal end and a distal end. A plurality of resilient fingers are formed on the body top to extend in a substantially distal direction from its distal end. Importantly, the body top is formed with a clear plastic window that is located between the proximal end of the body top and the distally-extending resilient fingers. To create the handle, the proximal end of the body top is bonded to the distal end of the handle body.

Another component of the safety catheter, the luer assembly, is the component that is used to actually establish the site for fluid access into the vasculature of the patient. Importantly, the luer assembly Includes a flexible cannula having a proximal end and a distal end. For the construction of the luer assembly, an eyelet is affixed to the proximal end of the cannula, and the eyelet is then fitted onto a hollow body portion. The purpose here is to hold the cannula on the body portion. With the eyelet fitted on the body portion of the luer assembly, the cannula extends distally from a distal end of the body portion. Additionally, a one-way valve is positioned on the body portion at a location that is proximal to the eyelet. The purpose of this one-way valve is to establish selective access to a fluid flow path that passes through the luer assembly from a proximal end of the body portion and through the cannula.

As mentioned above, in addition to the handle and the luer assembly, the safety catheter also includes a shuttle assembly. Structurally, the shuttle assembly includes a hollow, substantially tubular-shaped shuttle body that is molded from clear plastic. The shuttle body has a proximal end and a distal end, and it has an external surface that is formed with diametrically opposed flats that are located near the distal end of the shuttle body. Further, the shuttle body includes a hollow stylet having a sharp, beveled distal end, and it has a proximal end that is bonded to the distal end of the shuttle body.

Functionally, the shuttle assembly is mounted on the handle for movement from a first location, through the chamber of the handle body, to a second location inside the chamber. In this first location, the shuttle assembly is engaged with both the luer assembly and the handle. Specifically, the stylet of the shuttle assembly is inserted through the lumen of the cannula of the luer assembly in order to stiffen the cannula. Also, the luer assembly is fitted onto the handle and against the resilient fingers to urge the fingers of the handle against the flats of the shuttle assembly. This holds the shuttle assembly at the first location with the stiffened cannula extending in a distal direction from the handle. Accordingly, the stiffened cannula (catheter) of the luer assembly can be positioned in the vasculature of a patient.

To remove the stylet (i.e. shuttle assembly) from the cannula (i.e. luer assembly), and thereby affect a movement of the shuttle assembly from the first location to the second location, the luer assembly is simply separated from the handle. This separation then activates a spring mechanism inside the handle. In more structural detail, the shuttle assembly is formed with a lip, and the handle is formed with an abutment. With the shuttle in its first location, a spring is compressed between the lip of the shuttle assembly and the abutment of the handle. When the luer assembly is separated from the handle, however, the fingers of the handle are released from the shuttle assembly and the spring is thereby decompressed. As the spring expands, the shuttle assembly is repositioned to the second location inside the chamber. With this separation of the handle and shuttle assembly from the luer assembly, the luer assembly is left in place in the vasculature.

Prior to a use of the safety catheter of the present invention, a shield is engaged with the handle. Thus, when the shuttle assembly is at the first location, the shield covers the luer assembly. This is a protective measure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
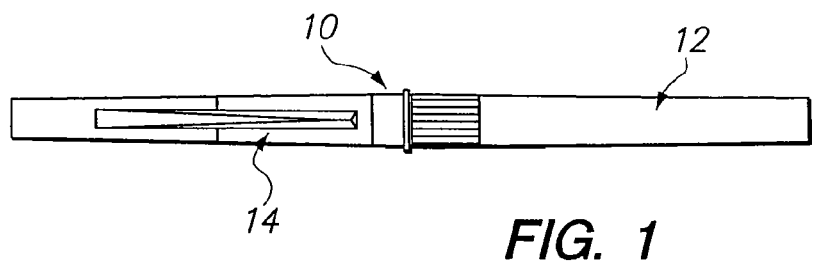
FIG. 1 is a straight-on side view of a safety catheter of the present invention.

Referring initially to FIG. 1, a safety catheter in accordance with the present invention is shown and is generally designated 10. More specifically, the safety catheter 10 is shown to include a handle 12 having a textured surface, and a shield (cap) 14. In FIG. 1 the shield 14 is shown engaged with the handle 12. With this engagement, ribs (not shown) that are located inside the shield 14 help stabilize components of the safety catheter 10 prior to its use. For an operational use of the safety catheter 10, however, the shield 14 is removed from the handle 12.

Figure 2:
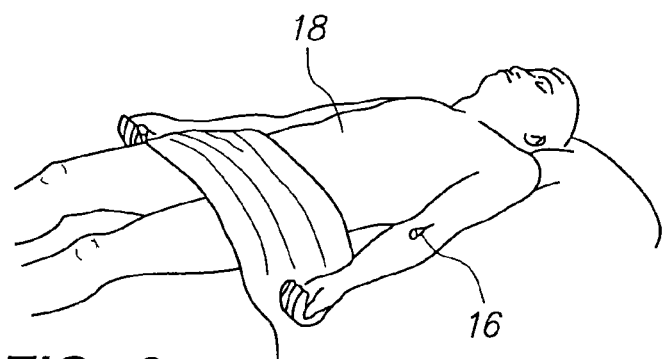
FIG. 2 is a view of a luer assembly of the safety catheter shown in its operational environment wherein the luer assembly is positioned to establish a site for fluid access into the vasculature of a patient.

In FIG. 2, a luer assembly 16, which is an essential component of the safety catheter 10, is shown positioned to establish fluid communication with the vasculature of a patient 18. As intended for the present invention, the luer assembly 16 is used to establish a single fluid-access site for repetitively or sequentially infusing fluid medicaments into the vasculature of a patient 18 from a fluid source (not shown).

Figure 3:
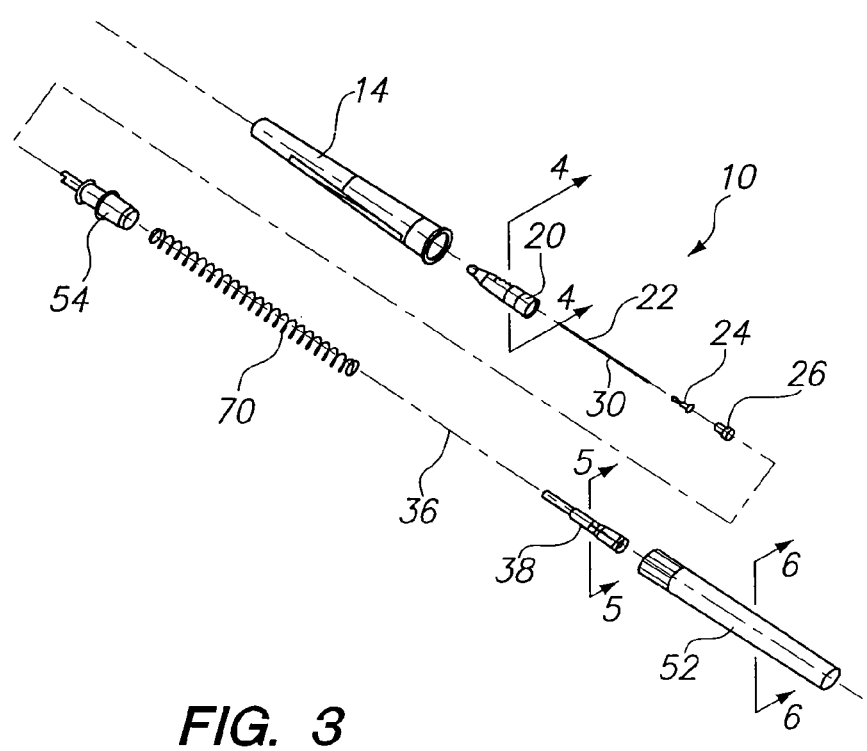
FIG. 3 is an exploded perspective view of the device shown in FIG. 1.

The exploded view of the safety catheter 10 that is shown in FIG. 3 illustrates the various component parts that are required for construction and assembly of the catheter 10. As shown, in addition to the shield 14, the safety catheter 10 includes a hollow body portion 20, a cannula 22, an eyelet 24, and a one-way valve 26. In combination, these particular parts establish the luer assembly 16. Further, it will also be seen that the body portion 20 has guides 28 which are formed in the hollow of the body portion 20.

Figure 4:
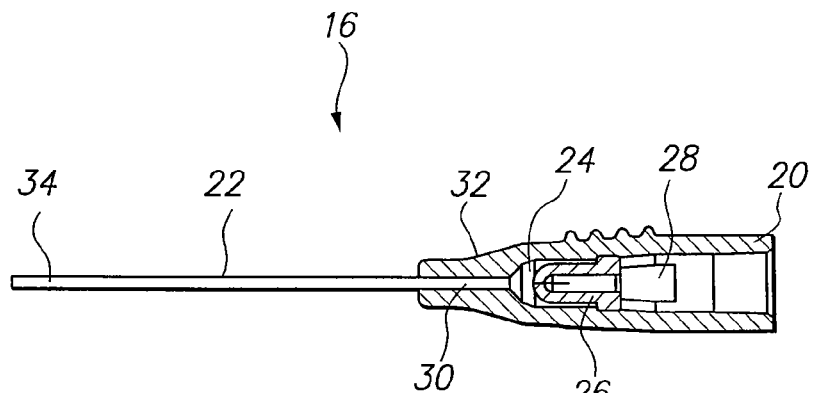
FIG. 4 is a cross section view of a luer assembly of the device as would be seen along the line 4-4 in FIG. 3.

In order to assemble the luer assembly, FIGS. 3 and 4 show that the proximal end 30 of the cannula 22 is bonded to the eyelet 24. The eyelet 24 is then fitted into the hollow body portion 20 so that the cannula 22 extends from the distal end 32 of the body portion 20, with its distal end 34 exposed. Also, as shown in FIG. 4, the luer assembly 16 includes a one-way valve 26 that is positioned at a location inside the hollow body portion 20, proximal to the eyelet 24. For the purposes of the present invention, the cannula 22 is preferably made of a flexible, bio-compatible elastomeric material.

Figure 5:
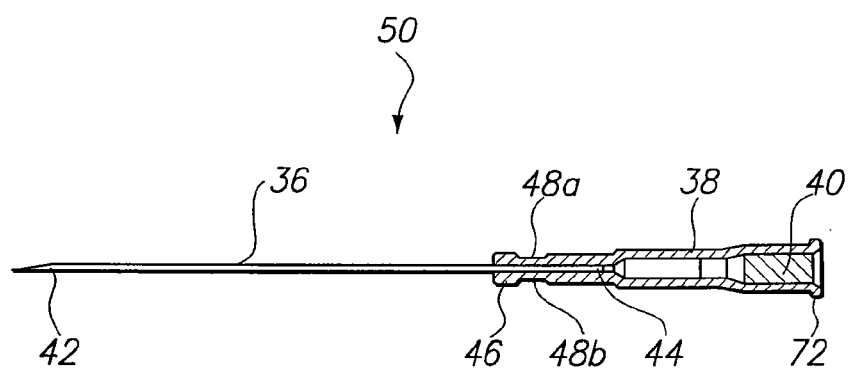
FIG. 5 is a cross section view of a shuttle assembly of the device as would be seen along the line 5-5 in FIG. 3.

Returning briefly to FIG. 3 it will be seen that the safety catheter 10 also includes a stylet 36 and a shuttle body 38. Further, in FIG. 5 it will be seen that a filter plug 40 is positioned inside the shuttle body 38. It will also be seen in FIG. 5 that the distal tip 42 of the stylet 36 is beveled to present a sharp end for penetrating tissue of the patient 18. And, the proximal end 44 of the stylet 36 is bonded to the distal end 46 of the shuttle body 38. FIG. 5 also shows that the distal end 46 of the shuttle body 38 is formed with diametrically opposed flats 48a and 48b. Together, and as shown in FIG. 5, the stylet 36 and the shuttle body 38, in combination with the filter plug 40, establish a shuttle assembly 50. For the present invention, the shuttle body 38 of the shuttle assembly 50 is preferably made of a clear plastic material.

Figure 6:
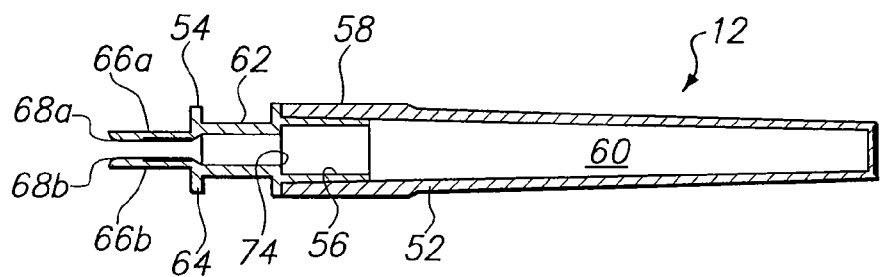
FIG. 6 is a cross section view of a handle assembly of the device as would be seen along the line 6-6 in FIG. 3.

With reference to FIG. 3 it is to be appreciated that the handle 12 of safety catheter 10 includes a handle body 52 and a body top 54. Structurally, the proximal end 56 of the body top 54 is bonded to the distal end 58 of the handle body 52. Further, as best seen in FIG. 6, the handle body 52 is formed with an internal chamber 60. Also, the body top 54 is formed with a window 62 that is located between the proximal end 56 and the distal end 64 of the body top 54. Importantly, the body top 54 is formed with a pair of resilient fingers 66a and 66b that extend in a distal direction from the distal end 64 of the body top 54. Each of the resilient fingers 66a and 66b is formed with a respective nib 68a and 68b. Additionally, a registration flat is formed at the distal end 64 to prevent rotation of the handle 12 when it is engaged with the shield (cap) 14. Preferably, the body top 54 is made of a clear plastic material.

FIG. 3 also shows that the safety catheter 10 includes a spring 70. More specifically, when the safety catheter 10 is assembled, the spring 70 is positioned between a lip 72 that is formed on the shuttle body 38 (see FIG. 5) and an abutment 74 that is formed inside the body top 54 (see FIG. 6). As intended for the present invention, the spring 70 is used to selectively provide a motive force that will change the configuration of the safety catheter 10 during its operation.

Operation

In the operation of the safety catheter 10 of the present invention, it is necessary that the shuttle assembly 50 be moved from a first location on the handle 12, to a second location inside the chamber 60 of the handle 12. More specifically, with the shuttle assembly 50 in its first location on the handle 12, the safety catheter 10 can be used to establish fluid access for the luer assembly 16 into the vasculature of the patient 18. To maintain this fluid access site, the luer assembly 16 needs to be effectively separated from the rest of the safety catheter 10. This is done by moving the shuttle assembly 50 to its second location inside the handle 12. Further, with the shuttle assembly 50 in its second location, the sharp distal tip 42 of the stylet 36 is effectively concealed inside the chamber 60 of the handle 12 to prevent inadvertent or accidental "sticks" by the stylet 36.

Figure 7:
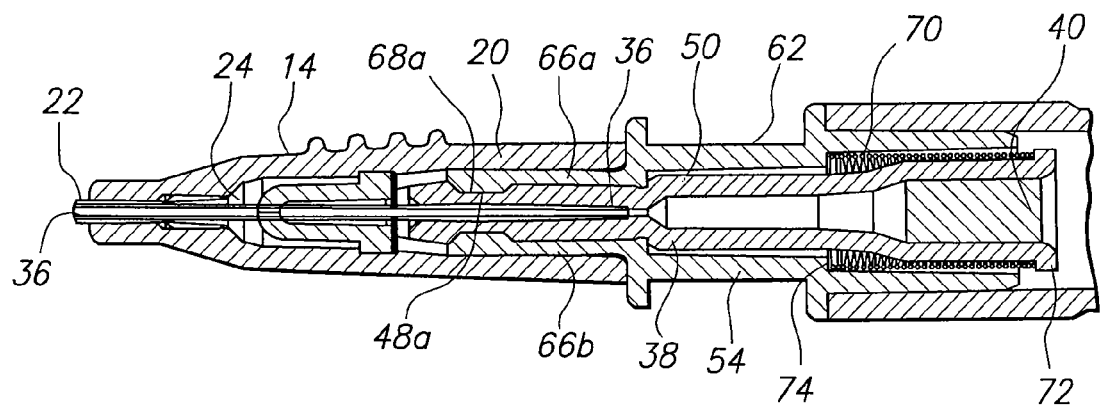
FIG. 7 is a cross section view of a combination of the respective assemblies shown in FIGS. 4, 5 and 6.
Figure 8:
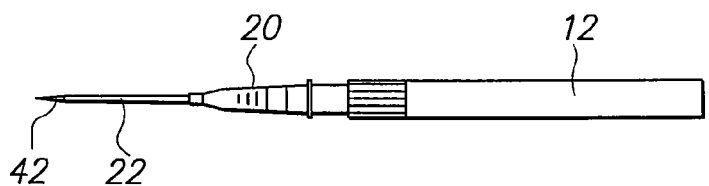
FIG. 8 shows a configuration for the device of the present invention with the shuttle assembly at a first location on the handle assembly.

Referring now to FIG. 7, when the shuttle assembly 50 is in its first location, the luer assembly 16, the shuttle assembly 50 and the handle 12 all interact with each other. In more detail, with the engagement of the shuttle assembly 50 to the luer assembly 16, the stylet 36 of the shuttle assembly 50 extends through the lumen in the cannula 22 of the luer assembly 16. This stiffens the cannula 22. At the same time, the guides 28 in the hollow body portion 20 of the luer assembly 16 register the stylet 36 of the shuttle assembly 50 with the luer assembly 14. Also, as the hollow body portion 20 of the luer assembly 16 is positioned over the resilient fingers 66a and 66b of the body top 54, the respective nibs 68a and 68b are aligned with flats 48a and 48b of the shuttle body 38 by the guides 28 of the luer assembly 16. This interaction between the luer assembly 16 and the handle 12 effectively holds the shuttle assembly 50 in its first location on the handle 12. A view of the safety catheter 10 when the shuttle assembly 50 is in its first location on the handle 12 is shown in FIG. 8. There it will be seen that the stiffened cannula 22 (i.e. as it is stiffened by the stylet 36) extends distally from the handle 12 for insertion of the cannula 22 into the vasculature of a patient 18 (see FIG. 2). It should also be noted that, as shown in FIG. 7, while the shuttle assembly 50 is in its first location, the spring 70 is compressed between the lip 72 on the shuttle body 38 and the abutment 74 on body top 54.

Figure 9:
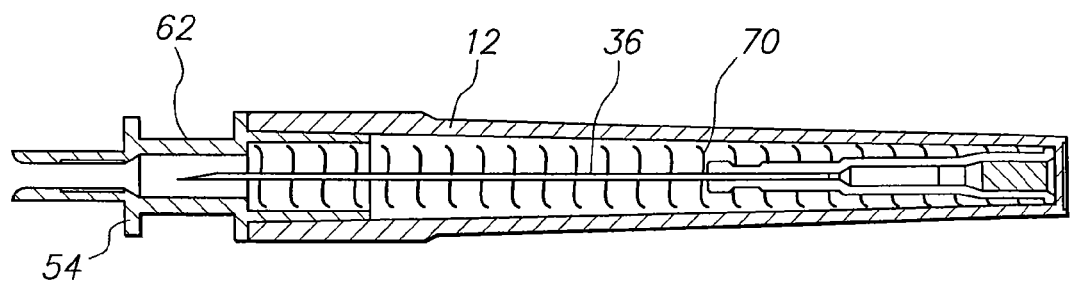
FIG. 9 shows a cross section view of a configuration for the present invention with the shuttle assembly at a second location on the handle assembly.

To confirm the safety catheter 10 has been properly positioned (i.e. the luer assembly 16 is in fluid communication with the vasculature of the patient 18), a blood "flash" can be observed through the window 62. The filter plug 40 then confines the blood that enters into the shuttle assembly 50 with this "flash", and prevents blood born pathogens from leaking out of the safety catheter 10. At this point, the luer assembly 16 can be disengaged from the handle 12. To do this, the hollow body portion 20 of the luer assembly 16 is lifted and removed from the resilient fingers 66a and 66b of the shuttle body 38. In turn, this causes the resilient fingers 66a and 66b of the handle 12 to be lifted from the flats 48a and 48b. This action disengages the body top 54 of the handle 12 from the shuttle assembly 50. At this point, the compressed spring 70 is no longer constrained. Thus, an expansion of the spring 70 then moves the shuttle assembly 50 through the internal chamber 60 to its second location on the handle 12 (see FIG. 9). Importantly, as a consequence of the above-described functionality, the luer assembly 16 remains in place in fluid communication with the vasculature of the patient 18 (see FIG. 2). Further, as best appreciated with reference to FIG. 9, the distal tip 42 of stylet 36 can be observed through the window 62 when the shuttle assembly 50 has been properly concealed within the chamber 60 of the handle 12.

While the particular Safety Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A safety catheter for use with a patient which comprises:
an elongated handle having a proximal end and a distal end, wherein the handle is formed with an internal chamber;
a hollow cylindrical-shaped body top made of a clear plastic and having a proximal end and a distal end, wherein the proximal end of the body top is bonded to the distal end of the handle, with a plurality of resilient fingers extending from the distal end of the body top, and wherein the body top is formed with a window between its proximal end and the fingers;
a hollow, substantially tubular-shaped shuttle body having a proximal end and a distal end and an external surface, wherein the external surface is formed with diametrically opposed flats near the distal end of the shuttle body;
a hollow stylet having a beveled distal end and a proximal end, with the proximal end bonded to the distal end of the shuttle body;
a luer assembly for establishing a site for fluid access into the vasculature of the patient, wherein the luer assembly includes a flexible cannula having a proximal and a distal end;
an eyelet, wherein the eyelet is affixed to the proximal end of the cannula for fluid communication therewith;
a hollow body portion, with the eyelet fitted into the body portion to hold the cannula thereon with the cannula extending distally from a distal end of the body portion;
a one-way valve positioned on the body portion proximal to the eyelet to selectively establish a fluid flow path through the luer assembly from a proximal end of the body portion and through the cannula; and
a shuttle assembly, wherein the shuttle assembly is mounted for movement on the handle from a first location to a second location, with the luer assembly fitted onto the handle to urge the fingers thereof against the shuttle assembly, to hold the shuttle assembly at the first location for insertion of the luer assembly into the patient, and for observation of a blood "flash" through the window to confirm proper positioning of the luer assembly, and further wherein the fingers of the handle are released from the shuttle assembly when the luer assembly is subsequently separated from the handle to reposition the shuttle assembly at the second location inside the chamber, for separation of the handle and shuttle assembly from the luer assembly and for observation of the distal end of the stylet through the window to confirm concealment of the stylet in the chamber of the handle and wherein the shuttle assembly is formed with a lip, and the handle is formed with an abutment, and the safety catheter further comprises a spring compressed between the lip of the shuttle assembly and the abutment of the handle with the window distal to the spring when the shuttle assembly is at the first location, and during movement of the shuttle assembly to the second location when the spring is decompressed as the fingers of the handle are released from the shuttle assembly.

2. A safety catheter as recited in claim 1 wherein the luer assembly includes a flexible cannula and the shuttle assembly includes the hollow stylet, wherein the hollow stylet of the shuttle assembly is inserted in the cannula of the luer assembly to stiffen the cannula when the shuttle assembly is held on the handle at the first location.

3. A safety catheter as recited in claim 1 further comprising a shield engageable with the handle to cover the luer assembly when the shuttle assembly is at the first location.

4. A method for positioning a flexible cannula in fluid communication with the vasculature of a patient which comprises steps of:

supporting the cannula with a one-way valve, wherein the cannula has a proximal end and a distal end, and the valve is unitary and is connected in fluid communication with the proximal end of the cannula for repetitive use, wherein the valve has an eyelet affixed to the proximal end of the cannula for fluid communication therewith and a hollow body portion, and wherein the eyelet is fitted into the body portion to hold the cannula thereon with the cannula extending distally from a distal end of the body portion, and wherein the valve is positioned on the body portion proximal to the eyelet to selectively establish a fluid flow path through a luer assembly from a proximal end of the body portion and through the cannula;

engaging a stylet with the valve for stiffening the flexible cannula, wherein the stylet is hollow and is mounted on a shuttle body having a proximal end and a distal end and an external surface, wherein the external surface is formed with diametrically opposed flats near the distal end of the shuttle body, and wherein the hollow stylet has a beveled distal end and a proximal end, with the proximal end bonded to the distal end of the shuttle body;

holding the stylet at a first location on a handle while the cannula is being positioned to establish fluid communication with the vasculature, wherein the stylet of the shuttle assembly is inserted through the cannula of the luer assembly to stiffen the cannula when the shuttle assembly is held on the handle at the first location, and wherein the handle comprises: a handle body formed with a chamber for concealing the shuttle assembly at the second location; wherein a proximal end of the body top is bonded to the distal end of the handle body with a plurality of resilient fingers extending from a distal end of the body top wherein the body top is made of a clear plastic and is formed with the window between the proximal end and the fingers, and;

observing a blood "flash" through an unobstructed window on the handle during the holding step of confirm the cannula has been properly positioned;

concealing the stylet at a second location in the handle when the valve is separated from the handle to leave the cannula and the valve in position for fluid communication with the vasculature; and observing the stylet through the unobstructed window the confirm the concealing step.

5. A method as recited in claim 4 wherein the shuttle assembly is formed with a lip, and the handle is formed with an abutment, and the method further comprises the steps of:

compressing a spring between the lip of the shuttle assembly and the abutment of the handle when the shuttle assembly is at the first location; and separating the handle from the valve to release the handle from the shuttle assembly for movement of the shuttle assembly into concealment at the second location in the handle.

* * * * *